United States Patent [19]

Otsuji et al.

[11] Patent Number: 5,208,209

[45] Date of Patent: May 4, 1993

[54] FLUORAN COMPOUNDS, PROCESS FOR PREPARATION THEREOF AND RECORDING MATERIALS COMPRISING SAID COMPOUND

[75] Inventors: Atsuo Otsuji, Kamakura; Masakatsu Nakatsuka; Kiyoharu Hasegawa, both of Yokohama; Masatoshi Takagi; Akihiro Yamaguchi, both of Kamakura, all of Japan

[73] Assignee: Mitsui Toatsu Chemicals, Inc., Tokyo, Japan

[21] Appl. No.: 810,095

[22] Filed: Dec. 19, 1991

Related U.S. Application Data

[62] Division of Ser. No. 584,219, Sep. 18, 1990, Pat. No. 5,087,706.

[30] Foreign Application Priority Data

Sep. 29, 1989 [JP] Japan ................................. 1-252054

[51] Int. Cl.$^5$ .......................... B41M 5/03; B41M 5/26; C07D 311/88
[52] U.S. Cl. ........................................ 503/221; 549/226
[58] Field of Search ........................... 549/226; 503/221

[56] References Cited

U.S. PATENT DOCUMENTS 4,910,183  3/1990  Dwyer-Hallquist et al. ...... 503/221
4,999,333  3/1991  Usami et al. ...................... 503/221

FOREIGN PATENT DOCUMENTS 176161  4/1986  European Pat. Off. .

Primary Examiner—C. Warren Ivy
Assistant Examiner—Ba K. Trinh
Attorney, Agent, or Firm—Millen, White, Zelano & Branigan

[57] ABSTRACT

Novel fluoran compounds represented by the formula (I):

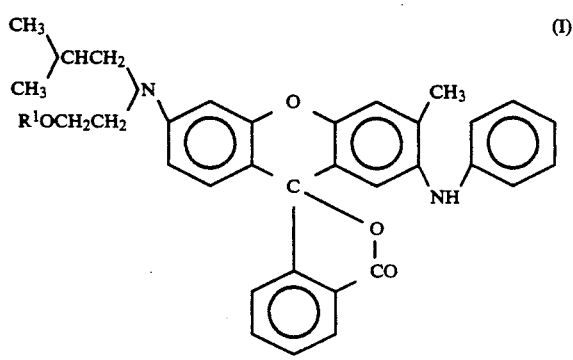

wherein $R^1$ is an alkyl group having from 1 to 4 carbon atoms, preparation process of the fluoran compounds, and a heat-sensitive and a pressure-sensitive recording material comprising the fluoran compound, are disclosed.

4 Claims, 1 Drawing Sheet

FLUORAN COMPOUNDS, PROCESS FOR PREPARATION THEREOF AND RECORDING MATERIALS COMPRISING SAID COMPOUND

This is a division of application Ser. No. 07/584,219 filed Sep. 18, 1990, now U.S. Pat. No. 5,087,706.

BACKGROUND OF THE INVENTION

1. Field of the Invention

The present invention relates to novel compounds which are useful as chromogenic compounds in recording materials such as pressure-sensitive and heat-sensitive recording materials, to a preparation process of these compounds, and to recording materials comprising these compound.

2. Description of the Prior Art

A color reaction between a colorless or pale colored electron donative compound (chromogenic compound) and an organic or inorganic electron acceptor (developer) has conventionally been utilized for pressure-sensitive recording, heat-sensitive recording and electroheat-sensitive recording as systems for recording transferred information through the mediation of external energy such as pressure, heat or electricity.

In these systems, fluoran compounds have widely been used as the chromogenic compound.

Many fluoran compounds are known in the prior art, for example, those having the formulas (A), (B), (C) and (D).

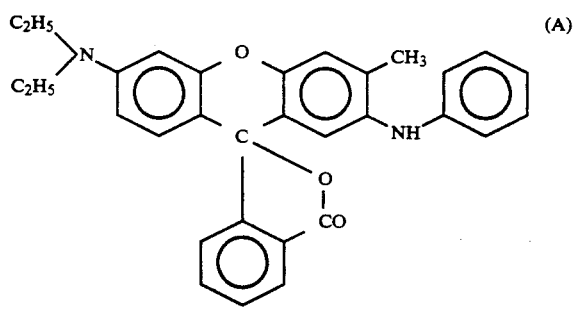

[Japanese Patent Publication SHO 48-43296(1973)]

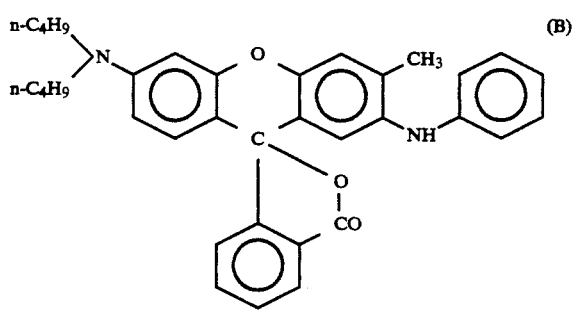

[Japanese Patent Publication SHO 48-43296(1973)]

[Japanese Patent Laid-Open Publication SHO 60-202155(1985)]

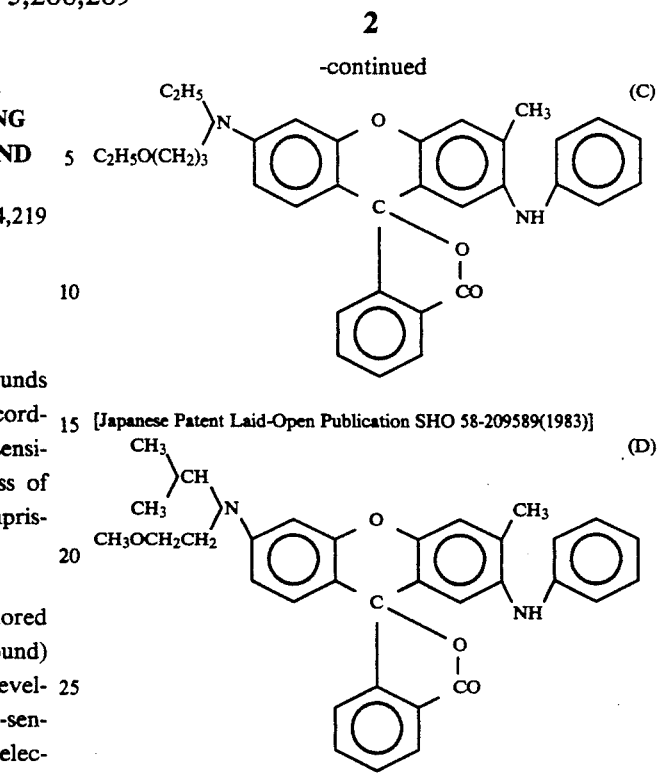

[Japanese Patent Laid-Open Publication SHO 58-209589(1983)]

However, the compound of the formula (A) has the disadvantage of very low solubility in capsule oil when the compound is used in a pressure-sensitive recording material. Additionally, in the case of applying to a heat-sensitive recording material, the compound colors gray to dark gray when mixed with a developer such as bisphenol A and has the defect of providing only a gray to dark gray colored (soiled) paper by applying the compound to a paper.

The coloring temperature of the compound of the formula (B) is too high to permit its use in a heat-sensitive recording material. Consequently, the performance of these prior art compounds cannot fully meet the present market demand for more rapid and higher density recording. Therefor, a chromogenic compound capable of quickly developing color at a lower temperature has been strongly desired.

Further, the compounds of the formulas (C) and (D) have caused serious disadvantage as the heat-sensitive recording material in practical use. For example, the heat-sensitive recording paper prepared by using these compounds has poor stability such as light stability and moisture resistance in preservation.

OBJECT OF THE INVENTION

The objects of the present invention are to provide novel fluoran compounds capable of meeting the current performance demands as a chromogenic compound for use in the recording materials, a process for preparing said compounds, and recording materials comprising the novel fluoran compounds of this invention.

SUMMARY OF THE INVENTION

One aspect of the present invention relates to novel fluoran compounds represented by Formula (I):

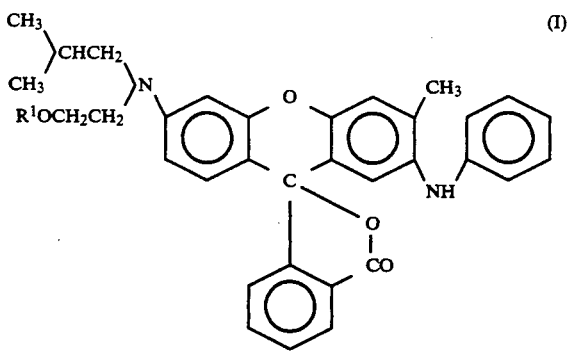

wherein R¹ is an alkyl group having from 1 to 4 carbon atoms.

Another aspect of the present invention relates to a process for the preparation of the fluoran compounds of this invention by reacting a benzoic acid derivative represented by Formula (II):

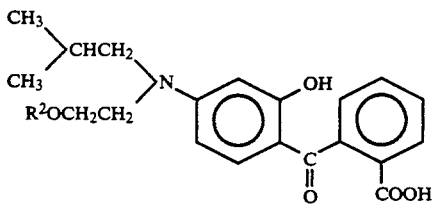

wherein R² is an alkyl group having from 1 to 4 carbon atoms, with a diphenylamine derivative represented by Formula (III):

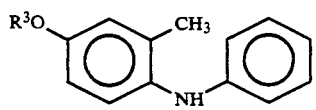

wherein R³ is a lower alkyl group.

A further aspect of the present invention relates to a recording materials comprising the fluoran compounds of the present invention.

BRIEF DESCRIPTION OF THE DRAWINGS

In the drawings.

In FIG. 1, curve (1) illustrates the color density characteristic of the fluoran compound of Formula (I) wherein R¹ is methyl, curve (2) illustrates that of the known fluoran compound having Formula (A), and curve (3) illustrates that of the known fluoran compound of Formula (B).

In FIG. 2, axis of abscissa indicates an angle of diffraction (2θ) and axis of ordinate indicates strength of diffraction.

DETAILED DESCRIPTION OF THE INVENTION

Figure 1:
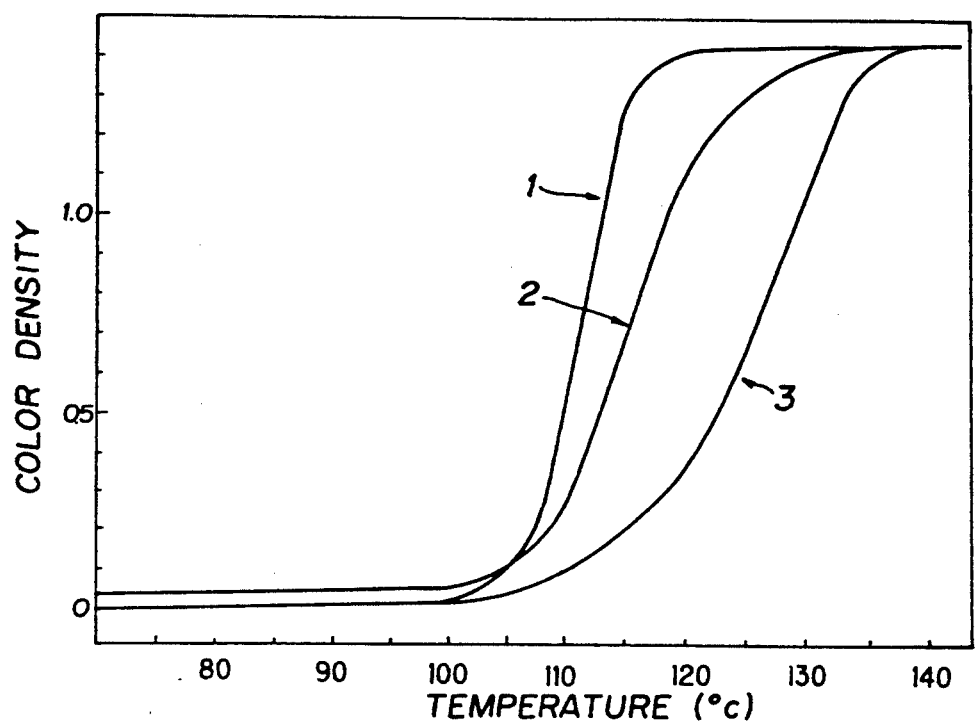
FIG. 1 illustrates color density characteristics to temperature change on the surface of heat-sensitive recording paper prepared by using a fluoran compound of the present invention and known fluoran compounds, respectively.

The fluoran compounds of the present invention are represented by the above Formula (I). R¹ in Formula (I) is an alkyl group having from 1 to 4 carbon atoms.

Exemplary alkyl group includes methyl, ethyl, n-propyl, isopropyl, n-butyl, isobutyl and sec-butyl. Particularly preferred alkyl groups are methyl, ethyl and n-butyl.

The fluoran compounds of the present invention can be prepared by reacting the benzoic acid derivative represented by the above Formula (II) with the diphenylamine derivative represented by the Formula (III) in the presence of a dehydrating condensation agent, for example, concentrated sulfuric acid, mixture of oleum and concentrated sulfuric acid, polyphosphoric acid, phosphorus pentaoxide and anhydrous aluminum chloride, preferably concentrated sulfuric acid, and thereafter bringing the reaction mixture to an alkaline pH.

The time and temperature of the dehydrating condensation reaction is not critical and is usually carried out at 0° to 100° C. for several hours to 100 hours. When the reaction is carried out in concentrated sulfuric acid, the preferred reaction temperature is in the range of 0° to 50° C.

The reaction time is dependent upon the selected reaction temperature and hence the reaction is conducted for a sufficient time to permit the reaction to go to completion.

After the dehydrating condensation is completed, the alkali treatment is usually carried out by the addition of a base, e.g., aqueous potassium hydroxide or sodium hydroxide solution to adjust the pH to an alkaline value, e.g., 9 to 12. The treatment can be conducted in the temperature range of 0° to 100° C. The alkali treatment may be conducted in the presence of an organic solvent, i.e., a solvent other than water, for example, benzene or toluene.

The benzoic acid derivative represented by Formula (II) which is used as a raw material in the present invention contains, as R² in Formula (II), an alkyl group having 1 to 4 carbon atoms, for example, methyl, ethyl, n-propyl, isopropyl, n-butyl, isobutyl and sec-butyl. Particularly preferred alkyl groups are methyl, ethyl and n-butyl.

Such derivative of benzoic acid can be typically prepared by reacting 3-N-isobutyl-N-2'-alkyloxyethylaminophenol with phthalic anhydride in the absence or presence of a solvent, such as benzene, toluene, xylene or tetrachloroethylene. A Lewis acid, such as zinc chloride, may also be added to the reaction.

Particularly preferred examples of the diphenylamine derivative represented by Formula (III) which is used as another raw material include compounds wherein R³ in Formula (III) is a lower alkyl group such as methyl or ethyl.

The recording material of the present invention is a pressure-sensitive recording material or heat-sensitive recording material comprising the fluoran compound of the present invention. In the recording material, the fluoran compound of the present invention is used singly or in combination as chromogenic compound. Further, in order to adjust the developed hue, other chromogenic compounds such as triphenylmethanelactones, fluorans and spiropyrans can also be added depending upon the demand.

When preparing pressure-sensitive recording materials, the fluoran compound represented by Formula (I) is dissolved in a solvent (capsule oil) which is generally used in the pressure-sensitive recording materials. The solvent includes a single solvent or a mixture selected from, for example, alkylbenzenes such as n-dodecylbenzene, alkylbiphenyls such as triethylbiphenyl and diisoproyldiphenyl, halogenated terphenyls, alkylnaphthalens such as diisopropyl naphthalene, diarylethanes such as phenylxylylethane and styrenated ethylbenzene, and chlorinated paraffins. The resulting solution is sealed by a coacervation method or an interfacial polymerization method into a microcapsule having an external wall comprised of gelatin, melamine-aldehyde resin, urea-aldehyde resin, polyurethane, polyurea, polyamide, or the like. Aqueous dispersion of the micro capsules is mixed with a suitable binder, such as starch paste and latex, and applied to a suitable substrate such as paper, plastic sheet or resin coated paper. The coated back sheet for pressure-sensitive recording is thus obtained.

The microcapsule dispersion obtained above can, of course, be used to produce so-called middle-sheets wherein the microcapsule dispersion is applied to one side of a substrate and a coating liquid primarily comprising a developer is applied to the other side of the substrate, and to produce so-called self contained sheets wherein both the microcapsules and the developer are present on the same side of a substrate.

The self contained sheet is prepared by applying a coating liquid comprising the microcapsules and the developer to one side of the substrate or by applying a microcapsules dispersion to one side of the substrate and then applying a coating liquid of the developer on the coated layer of microcapsules.

Exemplary developers suitable for use in the pressure-sensitive recording materials include copolymers of phenols and aldehydes such as formaldehyde; alkyl, aryl or aralkyl substituted salicylic acid such as 3,5-diamethylbenzylsalicylic acid; polycondensate of substituted salicylic acid and styrene; alkylphenols such as octylphenol; phenol aldehyde resin, such as p-phenylphenol novolak resin; metal salts of these compounds such as zinc, magnesium, aluminum, calcium, tin and nickel salts; and activated clays.

When preparing a heat-sensitive recording material of the invention, the fluoran compound represented by Formula (I) and a developer are pulverized in water to form an aqueous dispersion of fine particulates. Then binder is added to thus obtained dispersion.

Representative examples of developers which are suitable for use in the heat-sensitive recording material include bisphenol A, halogenated bisphenol A, alkylated bisphenol A, dihydroxydiphenyl sulfone, halogenated dihydroxydiphenyl sulfone, alkylated dihydroxydiphenyl sulfone, hydroxybenzoic acid esters, hydroquinone monoethers and other phenol derivatives; organic developers such as salicylic acid derivatives, salicylamide derivatives, urea derivatives, and thiourea derivatives; and inorganic developers such as acid clay, attapulgite, activated clay, aluminum chloride and zinc bromide.

Exemplary binder used for the heat-sensitive recording material includes polyvinyl alcohol, modified polyvinyl alcohol, methylcellulose, hydroxyethylcellulose, carboxymethylcellulose, gum arabic, salt of styrene-maleic anhydride copolymer, and isobutyleneacrylic acid-maleic anhydride copolymer.

Other additives can also be employed. Exemplary additives include fillers such as talc, kaolin and calcium carbonate, and if necessary, may also include sensitizers such as higher fatty acid amides, aromatic carboxylic acid esters, aromatic sulfonic acid esters, aromatic ethers, aromatic substituted aliphatic ethers, aromatic hydrocarbons, aromatic substituted aliphatic hydrocarbons and other generally known sensitizers for the heat-sensitive recording material; UV-absorbers; and defoamers.

The coating liquid obtained by the addition of the above additives can be applied to a suitable substrate such as paper, plastic sheet and resin coated paper, and used as the heat-sensitive recording material. The heat-sensitive recording system of the invention can of course be used in a solvent system without any problem in place of the above aqueous dispersion system. The system of the invention can also be employed for other enduse applications using chromogenic materials, for example, a temperature-indicating material.

When the fluoran compounds of Formula (I) in the present invention are used for the pressure-sensitive recording materials, the fluoran compounds can provide high solubility in capsule oil, an important property which is strongly desired for the chromogenic compound of pressure-sensitive recording materials. Further, the fluoran compounds of the present invention can develop an image having excellent light stability.

For example, the solubility of the fluoran compound of Formula (I), wherein $R^1$ is ethyl or n-butyl, in commercial capsule oils was compared with that of known fluoran compounds of the formulas (A) and (B), respectively. The results are shown in Table 1.

The method for determining solubility is as follows. Each compound was dissolved by heating at a concentration of 5% by weight in each oil. After standing at 5° C. for a week, the capsule oil is examined for precipitation of crystals.

TABLE 1

| Compound | SAS-296 | KMC-113 | SAS-296 80% IP 20% |
|---|---|---|---|
| Formula (I) $R^1$ = ethyl | ◯ | ◯ | ◯ |
| Formula (I) $R^1$ = n-butyl | ◯ | ◯ | ◯ |
| Formula (A) | X | X | X |
| Formula (B) | X | X | X |

Note: in table,
(1) ◯ means that no crystals are precipitated and X means that precipitation of crystals observed.
(2) SAS-296 is a capsule oil produced by Nippon Petrochemical Co., Ltd. and KMC-113 is a capsule oil produced by Kureha Chemical Co., Ltd. IP is isoparaffine.

As seen in Table 1, any of the fluoran compounds of the present invention represented by the formula (I) has higher solubility in each capsule oil as compared with known fluoran compounds of the formula(A) and formula(B).

These results mean that precipitation of crystals does not occur during storage in the capsule oil in the preparation of the pressure-sensitive recording material, and further that crystal precipitation in the microcapsules is not liable to occur after preparation of the microcapsules. This property is a remarkable characteristic of the fluoran compounds of the present invention.

Particularly, very good solubility in the mixture of SAS-296 and IP oil means availability of cheaper capsule oils, which circumstances are advantageous in economy and industry.

When the fluoran compounds of the present invention are used for the heat-sensitive recording materials, a heat-sensitive recording paper having a high whiteness without soil can be obtained. The heat-sensitive recording paper is extremely excellent in the preserving stability such as resistance to moisture and solvents, and can develop color at lower temperature as compared with those prepared by using the compounds of Formulas (A) and (B). Consequently, the fluoran compounds of the present invention have a very excellent performance in the present circumstances where rapid and highly-sensitive recording materials are desired.

For example, heat-sensitive recording papers prepared by using bisphenol A as a developer and the compound of Formula (I) wherein $R^1$ is methyl as chromogenic compound are compared with the heat-sensitive recording papers prepared by using bisphenol A as a developer and the compounds of Formulas (A), (C) and (D) as the chromogenic compound, respectively. The moisture and heat resistance and light stability of these heat-sensitive recording papers illustrated in Table 2.

The moisture and heat resistance test was carried out by holding the heat-sensitive recording papers at 60° C. in 90% relative humidity for 12 hours and thereafter by visually observing soil of papers.

The light stability test was carried out by irradiating UV-light for 4 hours on the above heat-sensitive recording papers by using a fade-meter and thereafter by visually observing the degree of yellowing of the recording papers.

TABLE 2

| Compound | Directly after application | Moisture and heat resistance | Light stability |
|---|---|---|---|
| Formula (I) $R^1$ = methyl | ◯ | ◯ | ◯ |
| Formula (A) | Δ | X | Δ |
| Formula (C) | Δ | X | Δ |
| Formula (D) | ◯ | X | X |

Note:
Evaluation directly after application and after the moisture and heat resistance test
◯ High whiteness without soil
Δ Somewhat soiled to gray
X Soiled to gray
Evaluation of light stability
◯ Almost no yellowing
Δ A little yellowing
▲ Considerable yellowing FIG. 1 illustrates color density characteristics to temperature change of the heat-sensitive recording papers prepared by using the fluoran compound of Formula (I) wherein $R^1$ is methyl, and the compounds of Formulas (A) and (B).

Color density was measured with a Macbeth reflection densitometer (Trade Mark: TR-524). Larger values indicate higher density of developed color.

As seen in FIG. 1, the compound of Formula (I) wherein $R^1$ is methyl develops color very quickly at about 100° C. Consequently, the compound of the present invention has a very excellent property that color development progresses quickly at lower temperatures as compared with the compounds of Formulas (A) and (B).

A means for adding a heat fusible material, i.e., sensitizer having a relatively low melting point of about 100° C. in addition to the chromogenic compound and the developer is commonly employed in order to develop color at lower temperatures. On the other hand, the heat-sensitive recording material prepared by using the compound of Formula (I) wherein $R^1$ is methyl has a remarkable advantage that color can be quickly developed at low temperature even though in the absence of the sensitizer or even though in the presence of a smaller amount of the sensitizer as compared with the case of using the compound of Formula (A) or (B).

The present invention will hereinafter be illustrated further in detail by way of examples. However, it is to be understood that the invention is not intended to be limited to the specific embodiments.

EXAMPLE 1

Preparation of the Compound of Formula (I) Wherein $R^1$ is Methyl

After dissolving 15.0 g of 2-(2'-hydroxy-4'-N-isobutyl-N-2"-methoxyethylaminobenzoyl)benzoic acid, i.e., the compound of Formula (II) wherein $R^2$ is methyl, in 100 ml of concentrated sulfuric acid at 10° C., 8.6 g of 4-methoxy-2-methyldiphenylamine, i.e., the compound of the formula (III) wherein $R^3$ is methyl, was added at the same temperature and stirred at 5° to 25° C. for 24 hours.

The reaction mixture was poured into 500 ml of ice water. The separated solid was collected, washed with water. The solid was added to a solvent mixture of 300 ml of toluene and 500 ml of 10% a aqueous sodium hydroxide solution, and stirred at 70° to 80° C. for 2 hours. Thereafter the toluene layer was separated, repeatedly washed with water until the washed water becomes neutral, and concentrated to about 10 ml. To the residue, 100 ml of methanol was added. The precipitated crystal was filtered and dissolved again in toluene. The toluene solution was treated with activated carbon, concentrated to about 10 ml and poured into 100 ml of methanol.

The precipitated crystal was filtered and dried to obtain 12.5 g of 3-(N-isobutyl-N-2'-methoxyethylamino)-6-methyl-7-anilinofluoran as almost colorless crystal. The yield was 58%. Melting point was 175° to 177° C.

A toluene solution of the compound thus obtained was colorless and transparent, and quickly developed a black color on silica gel.

Figure 2:
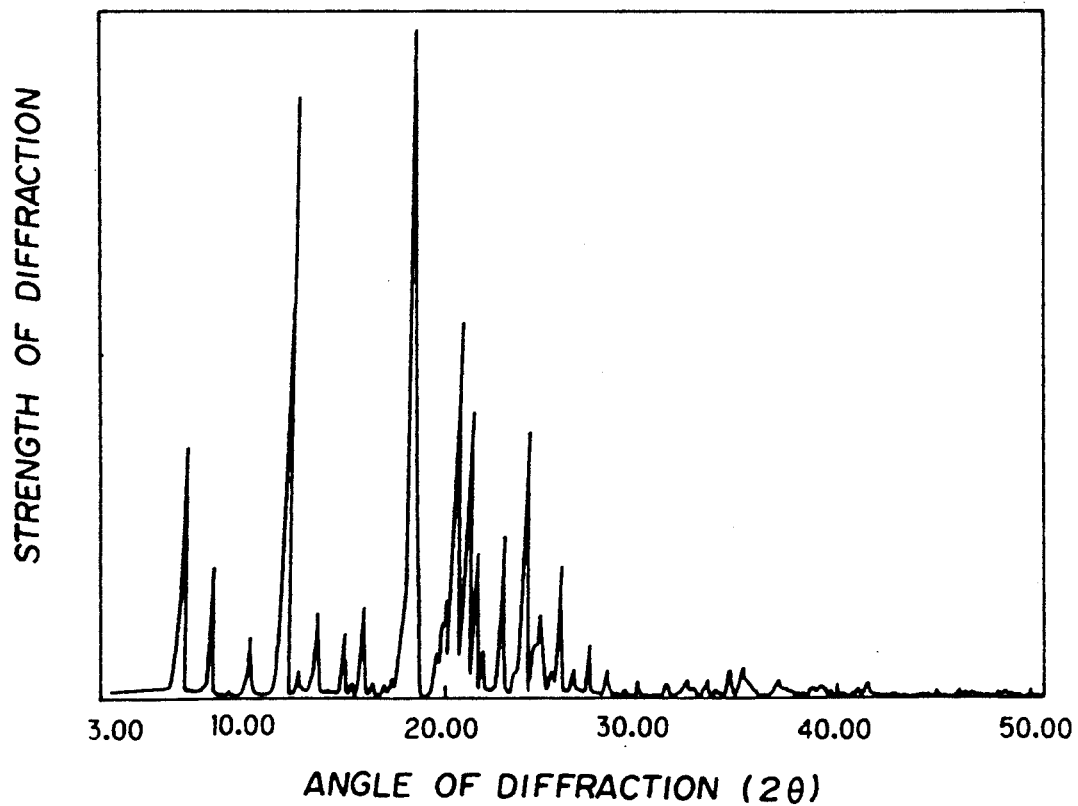
FIG. 2 is a X-ray diffraction diagram of the fluoran compound of Formula (I) wherein R¹ is methyl.

X-ray diffraction diagram of the crystal powder is illustrated in FIG. 2.

EXAMPLE 2

Preparation of the Compound of Formula (I) wherein $R^1$ is Ethyl

The same procedures as described in Example 1 were carried out except that 2-(2'-hydroxy-4'-N-isobutyl-N-2"-ethoxyethylaminobenzoyl)benzoic acid, the compound of Formula (II) wherein $R^2$ is ethyl, was used in place of 2-(2'-hydroxy-4'-N-isobutyl-N-2"-methoxyethylaminobenzoyl)benzoic acid. Thus 3-(N-isobutyl-N'-2-ethoxyethylamino)-6-methyl-7-anilinofluoran was prepared. Melting point was 98° to 100° C.

A toluene solution of the compound thus obtained was almost colorless and transparent, and quickly developed a black color on silica gel.

EXAMPLE 3

Preparation of the Compound of Formula (I) Wherein $R^1$ is n-butyl

The same procedures as described in Example 1 were carried out except that 2-(2'-hydroxy-4'-N-isobutyl-N-2"-n-butoxyethyl aminobenzoyl)benzoic acid, the compound of Formula (II) wherein $R^2$ is n-butyl, was used in place of 2-(2'-N-hydroxy-4'-N-isobutyl-N-2"-methoxyethylaminobenzoyl)benzoic acid. Thus 3-(N-isobutyl-N-2'-n-butoxyethylamino)-6-methyl-7-anilinofluoran was prepared.

Melting point was 112° to 115° C.

A toluene solution of the compound was almost colorless and transparent, and quickly developed a black color on silica gel.

EXAMPLE 4

Preparation of Heat-Sensitive Recording Paper Using the Compound of Formula (I) Wherein $R^1$ is Methyl A mixture of 10 g of 3-(N-isobutyl-N-2'-methoxyethylamino-6-methyl-7-anilinofluoran, 5 g of 10% aqueous polyvinyl alcohol solution and 37.5 g of water was pulverized to a particle size of 3μ using a sand mill.

Separately, bisphenol A was dispersed in a similar manner to obtain a 38% dispersion of developer.

The 65.8 g of the developer dispersion thus obtained, 50 g of aqueous dispersion of the above 3-(N-isobutyl-N-2'-methoxyethylamino)-6-methyl-7-anilinofluoran, 18.3 g of 60% aqueous precipitated calcium carbonate dispersion, 88 g of 10% aqueous polyvinylalcohol solution and 51.9 g of water were mixed.

The mixture obtained was applied on a white base paper using a wire rod No. 10 and air dried at room temperature to obtain an extremely white heat-sensitive recording paper which was free from soiling.

The heat-sensitive recording paper very quickly developed a black color by heating.

When the heat-sensitive recording paper was allowed to stand for 12 hours at 60° C. in a relative humidity of 60%, no soil was found on the paper at all as illustrated in Table 2.

The heat-sensitive recording paper was irradiated by UV-light for 4 hours by using a fade-meter and almost no yellowing was observed on the paper as illustrated in Table 2.

Color density characteristic of the paper depending upon temperature change was measured by using a color development tester (RHODIACETA). Result are illustrated in FIG. 1.

COMPARATIVE EXAMPLE 1

The same procedures as described in Example 4 were carried out except that 3-(N-isobutyl-N-2'-methoxyethylamino)-6-methyl-7-anilinofluoran was replaced by 3-N,N-diethylamino-6-methyl-7-anilinofluoran, the compound of the formula (A); 3-N,N-di-n-butylamino-6-methyl-7-anilinofluoran, the compound of the formula (B); 3-(N-ethyl-N-3'-ethoxypropylamino)-6-methyl-7-anilinofluoran, the compound of the formula (C); or 3-(N-isopropyl-N-2'-methoxyethylamino)-6-methyl-7-anilinofluoran, the compound of the formula (D).

Each heat-sensitive recording paper was thus prepared.

Coated surface of the heat-sensitive recording paper prepared by using the compound of the formula (A) or (C) was somewhat gray colored and soil was found.

The heat-sensitive recording papers prepared respectively by using the compound of the formula (A), (C) and (D) were irradiated with UV-light for 4 hours by using a fade-meter. Yellowing was found on any paper as illustrated in Table 2.

Also, these heat-sensitive recording papers was allowed to stand at 60° C. for 12 hours in relative humidity of 90%. The coated surface of any paper was soiled to gray as illustrated in Table 2.

Color density characteristic to temperature change on the heat-sensitive recording papers prepared respectively by using the compound of the formula (A) and (B) was measured using a RHODIACETA.

Result are illustrated in FIG. 1.

EXAMPLE 5

Preparation of Pressure-Sensitive Recording Paper by Using the Compound of Formula (I) Wherein $R^1$ is Ethyl Coating back sheet (CB) and coating front sheet (CF) were prepared by the following procedures.

A mixture of 100 g of 10% aqueous solution of ethylenemaleic anhydride copolymer and 240 g of water was adjusted to pH 4.0 by the addition of a 10% aqueous sodium hydroxide solution. To the mixture, 200 g of a 5 wt % solution of 3-(N-isobutyl-N-2'-ethoxyethylamino)-6-methyl-7-anilinofluoran in phenylxylethane (Trade Mark; SAS-296, a product of Nippon Petrochemical Co. Ltd. was added and emulsified with a homomixer. Thereafter 60 g of an aqueous methylolmelamine solution containing 50% of solid (Trade Mark; Uramine T-30, a product of Mitsui Toatsu Chemicals Inc.) was added and maintained at 55° C. for 3 hours with stirring to obtain a microcapsule dispersion having an average particle size of 5.0μ.

To 100 g of the microcapsule dispersion, 40 g of wheat starch, 20 g of 20% paste of oxidized starch and 116 g of water, were added and dispersed. The resultant dispersion was applied as a coating on a paper having a basis weight of 40 g/m$^2$ so as to obtain a coating weight of 5 g/m$^2$ as solid. CB sheet was thus obtained.

In order to prepare CF sheet, the zinc salt of a substituted salicylic acid-styrene copolymer was pulverized in water with a sand grinding mill in the presence of a small amount of a high molecular weight anionic surfactant to obtain an aqueous dispersion containing 40% by weight of solid. Using the aqueous dispersion, an aqueous coating compound (30% solid content) having the below described composition was prepared and applied on a wood free paper having a basis weight of 40 g/m$^2$ so as to obtain a coating weight of 5.5 g/m$^2$. CF sheet was thus obtained.

| Composition of aqueous coating compound | Weight of solid (g) |
| --- | --- |
| Precipitated calcium carbonate | 100 |
| Developer | 20 |
| Adhesive (Oxidized starch) | 8 |
| Adhesive (Synthetic latex) | 8 |

The microcapsule coated CB sheet and the developer coated CF sheet were overlapped so as to bring both coated surfaces into contact with each other. When pressure was applied on the stacked sheets with a pencil, black image was emerged on the developer coated surface. The developed color image had with respect to problem on resistance to light, moisture and NOx in practical use.

EXAMPLE 6

Preparation of Pressure Sensitive Recording Paper Using the Compound of the Formula (I) Wherein $R^1$ is n-butyl A CB sheet and a CF sheet were prepared carrying out the same procedures as described in Example 5 except that 3-(N-isobutyl-N-2'-ethoxyethylamino)-6-methyl-7-anilinofluoran was replaced by 3-(N-isobutyl-N-2'-n-butoxyethylamino)-6-methyl-7-anilinofluoran.

Color image was developed by conducting the same procedures as described in Example 5.

The developed image had no problem with respect to resistance to light, moisture and NOx in practical use.

What is claimed is:

1. A recording material comprising the fluoran compound represented by the formula (I)

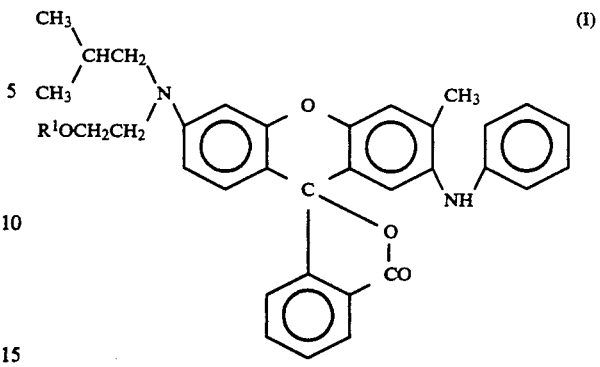

wherein $R^1$ is an alkyl group having from 1 to 4 carbon atoms.

2. A heat-sensitive recording material of claim 1 wherein in the fluoran compound of formula (I), $R^1$ is methyl.

3. A pressure-sensitive recording material of claim 1, wherein in the fluoran compound of formula (I), $R^1$ is ethyl.

4. A pressure-sensitive recording material of claim 1, wherein in the fluoran compound of formula (I), $R^1$ is butyl.

* * * * *